(12) United States Patent
Schweiger et al.

(10) Patent No.: US 6,626,986 B2
(45) Date of Patent: Sep. 30, 2003

(54) LOW-TEMPERATURE-SINTERING POTASSIUM-ZINC-SILICATE GLASS

(75) Inventors: Marcel Schweiger, Chur (CH); Volker Rheinberger, Vaduz (LI); Wolfram Höland, Schaan (LI)

(73) Assignee: Ivoclar Vivadent AG (LI)

( * ) Notice: Subject to any disclaimer, the term of this patent is extended or adjusted under 35 U.S.C. 154(b) by 114 days.

(21) Appl. No.: 09/887,308

(22) Filed: Jun. 22, 2001

(65) Prior Publication Data

US 2002/0035025 A1 Mar. 21, 2002

Related U.S. Application Data

(60) Provisional application No. 60/245,871, filed on Nov. 3, 2000.

(30) Foreign Application Priority Data

Jun. 28, 2000 (DE) .......................................... 100 31 431

(51) Int. Cl.$^7$ ............................ C03C 3/078; A61K 6/00
(52) U.S. Cl. ............................. 106/35; 501/57; 501/58; 501/59; 501/63; 501/64; 501/70; 501/72
(58) Field of Search ............................. 106/35; 501/57, 501/58, 59, 63, 64, 67, 69, 70, 72

(56) References Cited

U.S. PATENT DOCUMENTS

| | | | |
|---|---|---|---|
| 5,618,763 A | 4/1997 | Frank et al. | |
| 5,641,347 A | 6/1997 | Grabowski et al. | |
| 5,968,856 A | 10/1999 | Schweiger et al. | |
| 6,121,175 A | 9/2000 | Drescher et al. | |

FOREIGN PATENT DOCUMENTS

| | | |
|---|---|---|
| EP | 0 885 855 A2 | 5/1998 |
| EP | 0 916 625 A1 | 11/1998 |
| GB | 2 320 023 A | 6/1998 |

*Primary Examiner*—C. Melissa Koslow
(74) *Attorney, Agent, or Firm*—Nixon Peabody LLP

(57) ABSTRACT

Potassium-zinc-silicate glasses are described which because of their high chemical stability as well as their optical properties and favorable working properties are suitable in particular as coating or veneering materials for ceramic dental suprastructures and thus for the preparation of all-ceramic dental restorations, such as crowns or bridges.

24 Claims, No Drawings

LOW-TEMPERATURE-SINTERING POTASSIUM-ZINC-SILICATE GLASS

This application claims the benefit of U.S. Provisional Patent Application No. 60/245,871, filed Nov. 3, 2000, which is herein incorporated by reference in its entirety.

The invention relates to potassium-zinc-silicate glass and particularly that which can be processed at low temperatures by sintering and is particularly suitable for the desired establishment of the optical properties and the processing properties of coating and veneering material for ceramic dental restorations.

Apart from metalic dental restorations which, for aesthetic reasons, are veneered with ceramic layers, all-ceramic restorations, in which a ceramic veneering or coating material is also applied to a core made from ceramic material, are increasingly used in dentistry. Glass ceramics can be considered amongst others for use as core and also as coating material.

Above all, the optical properties as well as the working properties of glass ceramic coating material are however frequently unsatisfactory. Thus as a result of their high crystal content, the glass ceramics used show a pronounced turbidity, which is not acceptable especially in the case of dental restorations for the incisor region. Moreover, in many cases, the glass ceramics have a very high coefficient of expansion, which is why they are unsuitable as coating material for cores made from glass ceramic with a low coefficient of expansion, such as e.g. lithium disilicate glass ceramic. As a result of the inadequate matching of the coefficients of expansion, undesired separation of the coating material may result.

It is furthermore known that leucite-containing glass ceramics themselves have very high linear thermal coefficients of expansion. These are due to the level of leucite crystals, which are formed by the controlled crystallization of a corresponding starting glass.

Alkali-zinc-silicate glasses are known from EP-A-695 726, which are suitable for veneering mainly metal dental suprastructures, but can contain only 8.0 wt.-% ZnO at most, which is why their chemical resistance is still not satisfactory in every case. With thermal treatment in the range of 600° C. to 1000° C. and thus under processing conditions usual for the dental technician, the glasses furthermore form corresponding glass ceramics which are pronouncedly clouded as a result of their crystal content and are thus not suitable for establishing a high translucence in a glass ceramic coating material. The level of crystals, in particular leucite, also leads to undesirably high sintering temperatures and coefficients of expansion, so that they are not satisfactory for the veneering of ceramic substrates with low coefficients of expansion.

Alkali-silicate glasses are known from EP-A-885 606 which can be used as dental coating or veneering materials. However they contain 5.0 wt.-% of ZnO at most and are characterized inter alia by a $K_2O$ content of only 8.5 wt.-% at most. Consequently, the chemical resistance of these glasses is not sufficient in every case and they still have rather high sintering temperatures.

Even if the known glasses already show good results when used as components for veneering and coating materials, coatings on thin frameworks made from glass ceramics cannot however be manufactured with them without cracks forming. As a rule, the result in these thin layered composites is a build-up of stress and thus a cracking-off of the applied coating material or a fracture of the completed dental restoration. A further reason for this behaviour is the sintering temperatures of the known glasses which are still rather high. Thus the preparation of veneers, thin-valled veneers or thin-walled crowns with a glass ceramic core is not possible with them.

Furthermore, the satisfactory processing of the known glasses by sintering is possible only in a narrow temperature range. When there are larger deviations from the actual sintering temperature, these glasses show an unsatisfactory dimensional stability in the case of too high a temperature and an unacceptably high porosity in the case of too low a temperature after sintering. The satisfactory workability only in a narrow temperature range is very disadvantageous, as the furnaces used for the preparation of dental restorations are small, and it is thus generally difficult to constantly maintain a desired temperature in them over a certain period of time. Particularly in furnaces which operate at low temperatures, such as lower than 850° C., considerable fluctuations in temperature occur during a sintering process.

The object of the invention is therefore to provide a glass which has a low coefficient of expansion, a low sintering temperature, a high chemical resistance as well as a high translucence and the chemical composition of which is compatible in particular with that of apatite glass ceramics and lithium disilicate glass ceramics, so that a strong bond can be formed between the glass and the glass ceramic and the glass is thus suitable for the preparation of coatings or veneers for thin-walled dental restorations. Furthermore, the glass is to be processable into the desired restorations in a wide temperature range.

This object is achieved by means of the potassium-zinc-silicate glass according to the present invention.

The subject-matter of the present invention is also the dental material, the use as well as the shaped dental product according to the invention.

The potassium-zinc-silicate glass according to the invention comprises the following components:

| Component | wt.-% |
|---|---|
| $SiO_2$ | 60.0 to 72.0 |
| $Li_2O$ | 1.0 to 5.0 |
| $K_2O$ | 10.0 to 23.0 |
| ZnO | 8.5 to 20.0 |

The glass according to the invention can additionally comprise at least one of the following components:

| Component | wt.-% |
|---|---|
| $Na_2O$ | 0 to 4.0 |
| MgO | 0 to 4.0 |
| CaO | 0 to 3.6 |
| SrO | 0 to 3.0 |
| $Al_2O_3$ | 0 to 8.0 |
| $B_2O_3$ | 0 to 3.3 |
| $La_2O_3$ | 0 to 3.0 |
| $ZrO_2$ | 0 to 6.0 |
| $TiO_2$ | 0 to 2.5 |
| $CeO_2$ | 0 to 2.0 |
| $SnO_2$ | 0 to 5.0 |
| $P_2O_5$ | 0 to 1.0 |
| $Tb_4O_7$ | 0 to 1.8 |
| F | 0 to 1.1. |

If these additional components are present, they are used in particular in amounts of at least 0.1 wt.-%. For the individual components of the potassium-zinc-silicate glass according to the invention, there are preferred quantity ranges. These can be selected independently of each other and are as follows:

| Component | wt.-% |
| --- | --- |
| $SiO_2$ | 62.0 to 70.0 |
| $Li_2O$ | 2.0 to 5.0 |
| $K_2O$ | 10.0 to 20.0 |
| $ZnO$ | 10.0 to 19.0 |
| $Na_2O$ | 0 to 3.0 |
| $MgO$ | 0 to 3.0 |
| $CaO$ | 0 to 3.0 |
| $SrO$ | 0 to 3.0 |
| $Al_2O_3$ | 0 to 6.0 |
| $B_2O_3$ | 0 to 3.0 |
| $La_2O_3$ | 0 to 2.0 |
| $ZrO_2$ | 0 to 5.0 |
| $TiO_2$ | 0 to 2.0 |
| $CeO_2$ | 0 to 1.5 |
| $SnO_2$ | 0 to 4.0 |
| $P_2O_5$ | 0 to 0.8 |
| $Tb_4O_7$ | 0 to 1.0 |
| F | 0 to 1.0. |

Particularly preferred quantity ranges for the individual components of the glass according to the invention are as follows, and these can also be selected independently of each other:

| Component | wt.-% |
| --- | --- |
| $SiO_2$ | 63.0 to 69.0 |
| $Li_2O$ | 3.0 to 5.0 |
| $K_2O$ | 11.0 to 19.0 |
| $ZnO$ | 10.0 to 17.0 |
| $Na_2O$ | 0 to 2.5 |
| $MgO$ | 0 to 2.5 |
| $CaO$ | 0 to 2.5 |
| $SrO$ | 0 to 2.5 |
| $Al_2O_3$ | 0 to 4.0 |
| $B_2O_3$ | 0 to 2.0 |
| $La_2O_3$ | 0 to 1.8 |
| $ZrO_2$ | 0 to 4.0 |
| $TiO_2$ | 0 to 1.8 |
| $CeO_2$ | 0.1 to 1.5 |
| $SnO_2$ | 0 to 3.5 |
| $P_2O_5$ | 0 to 0.5 |
| $Tb_4O_7$ | 0 to 0.8 |
| F | 0 to 0.8. |

All the above quantity amounts in wt.-% relate to the glass.

For the preparation of the glass according to the invention the preferable procedure is to melt suitable starting materials, such as e.g. carbonates, oxides and fluorides, at a temperature in the range of 1350° C. to 1650° C., preferably 1400° C. to 1600° C., over a period of time of 30 minutes to 4 hours, preferably 1 hour to 2.5 hours, with formation of a homogenous melt. The melted glass is then normally quenched in water, i.e. fritted, and after being dried is ground to the desired particle size.

By means of scanning electron microscopic studies, it was established that the glass according to the invention is free from crystals. It was further shown that the glass also survives the conditions which prevail in the case of a customary additional dental processing by sintering, without there resulting a formation of crystals such as occurs with known glasses. Even with a thermal treatment in the range of 600° C. to 800° C. for 1 minute to 1 hour, there was no crystallization.

The glass according to the invention normally has a very advantageous sintering temperature of less than 800° C. during sintering onto a ceramic or glass-ceramic substrate, such as a lithium disilicate glass ceramic. Glasses are particularly preferred which have a sintering temperature of 760° C. and below and thus can be processed at this temperature. These low sintering temperatures are presumably attributable to the special composition of the glass according to the invention.

It is of quite particular advantage that the glass according to the invention can also be processed by sintering even where there are large deviations from the actual sintering temperature, i.e. the temperature at which the dimensional stability as well as the porosity of the glass are particularly satisfactory. Thus the glass can even be processed in a sintering temperature range of ±20° C., or more, such as e.g. ±40° C., above or below the actual sintering temperature without cracks or faults occurring in the dental restoration. When working in this temperature range, the sintered glass has a very low porosity and a very good dimensional stability. An indication of the excellent dimensional stability is that even the very thin-walled incisor edge, which has been formed by applying a mixture of glass powder and admixing liquid to a framework as well as its shaping, retains its form after the sintering process and thus lasts. Thus, the glass according to the invention can also be sintered in furnaces which do not permit a precise control of the firing temperature, which is particularly advantageous. In contrast to this, conventional glasses permit only deviations of ±10° C. from the sintering temperature. With larger deviations, satisfactory restorations cannot be prepared with them.

In order to carry out the sintering of the glass according to the invention, a heating-up rate of 3° C. to 100° C./min and preferably of 30° C. to 80° C./min as well as a holding time at the sintering temperature of 10 seconds to 1 hour and preferably 30 seconds to 5 minutes is selected as a rule. It is advantageous to carry out the sintering in a vacuum so that the sintered body has as few a pores as possible.

The linear thermal coefficient of expansion of the glass according to the invention is normally less than $12.3 \times 10^{-6}$ $K^{-1}$, preferably 7.7 to $10.9 \times 10^{-6}$ $K^{-1}$, measured in the temperature range from 100° C. to 400° C.

The glass according to the invention is preferably used as dental material either on its own or together with further components. To this end, it is usually used in the form of a powder with an average particle size of less than 90 μm. Glass ceramics and other glasses, but also dyestuffs, in particular color pigments, oxides of the 3d elements or metal colloids, as well as fluorescence materials, in particular ytterbium silicate doped with d- and f-elements, can also be considered as further components.

Dental material which contains at least one glass ceramic and preferably an apatite glass ceramic as a further component is particularly advantageous.

An apatite glass ceramic is preferred which comprises the following components and in which the main crystal phase is formed by apatite crystals:

| component | wt.-% |
| --- | --- |
| $SiO_2$ | 56.0 to 65.0 |
| $Li_2O$ | 1.8 to 5.3 |
| $K_2O$ | 9.0 to 17.5 |
| ZnO | 9.0 to 16.0 |
| CaO | 3.5 to 10.5 |
| $P_2O_5$ | 2.0 to 6.0 |
| F | 0.5 to 1.0 |

This apatite glass ceramic particularly preferably comprises in addition at least one of the following components:

| Component | wt.-% |
| --- | --- |
| $Na_2O$ | 0 to 5.0 |
| MgO | 0 to 3.5 |
| SrO | 0 to 3.5 |
| $Al_2O_3$ | 0 to 6.0 |
| $B_2O_3$ | 0 to 2.0 |
| $La_2O_3$ | 0 to 3.0 |
| $ZrO_2$ | 0 to 7.5 |
| $TiO_2$ | 0 to 7.5 |
| $CeO_2$ | 0 to 2.0 |
| $SnO_2$ | 0 to 5.0 |
| $Tb_4O_7$ | 0 to 0.5. |

The above amounts in wt.-% relate to the apatite glass ceramic. If these additional components are present, they are used in particular in amounts of at least 0.1 wt.-%.

The apatite glass ceramics are prepared by melting a starting glass from suitable starting materials, such as oxides, carbonates and fluorides, at temperatures from 1200° C. to 1650° C., pouring this into water and subjecting the formed glass granulate, optionally after further reduction, to a thermal treatment at more than 500° C. and up to 900° C. for a period of 30 minutes to 6 hours.

The obtained apatite glass ceramics are characterized by a high translucence, high chemical resistance as well as a low coefficient of expansion. They are moreover excellently matched in their chemical composition to the glasses according to the invention, so that disadvantageous material transport reactions between both materials and thus ensuing build-up of stress are avoided in particular in thin layered composites.

The dental material according to the invention normally has a linear thermal coefficient of expansion of 9.0 to $10.9 \times 10^{-6}$ $K^{-1}$, measured in the range of 100° C. to 400° C. The respectively desired coefficient can be set by suitable choice of the type of potassium-zinc-silicate glass and any further components, as well as their amounts. Favourable dental materials contain 10 to 90 wt.-% potassium-zinc-silicate glass and 90 to 10 wt.-% further components, relative to the dental material.

The dental material according to the invention is suitable for coating substrates and in particular for coating or veneering dental restorations. The coating takes place in particular by applying the dental material to the selected substrate and subsequent sintering at less than 800° C. and in particular 760° C. or less.

Preferably a powder of the glass according to the invention is firstly mixed with a powder of the optionally present further components and processed to a paste by adding aqueous admixing solutions. This paste is then applied to the substrate and after desired shaping sintering takes place in order to obtain a firmly adhering coating or veneer.

The dental material according to the invention can be used as coating or veneering material for substrates such as dental suprastructures e.g. based on ceramic or glass ceramic materials. Due to its low coefficient of expansion, it is preferably used for substrate materials with a thermal coefficient of expansion of 7.0 to 12.0, in particular 8.0 to $11.0 \times 10^{-6}$ $K^{-1}$. It is preferably used for coating or veneering $ZrO_2$ ceramics, $Al_2O_3$ ceramics, $ZrO_2/Al_2O_3$ ceramics, ceramic or glass ceramic composite materials and titanium.

It is particularly advantageously used however to veneer substrates based on lithium disilicate glass ceramic in order to in this way prepare aesthetically very attractive all-ceramic dental products which have a very high strength as well as an excellent chemical resistance.

Lithium disilicate glass ceramics which contain the components listed below and which can be obtained e.g. by melting of suitable starting glasses, fritting and thermal treatment at 400° C. to 1100° C., have proved particularly suitable:

| Component | wt.-% |
| --- | --- |
| $SiO_2$ | 57.0 to 80.0 |
| $Al_2O_3$ | 0 to 5.0 |
| $La_2O_3$ | 0.1 to 6.0 |
| MgO | 0 to 5.0 |
| ZnO | 0 to 8.0 |
| $Li_2O$ | 11.0 to 19.0 |
| $P_2O_5$ | 0 to 11.0 | where
 (a) $Al_2O_3+La_2O_3$ account for 0.1 to 7.0 wt.-% and
 (b) MgO+ZnO account for 0.1 to 9.0 wt.-%.

The amounts in wt.-% relate to the lithium disilicate glass ceramic.

The potassium-zinc-silicate glass according to the invention and the dental material according to the invention can be processed into shaped dental products in the usual way together with the optionally present additives. Dental restorations such as e.g. an inlay, an onlay, a bridge, a stump reconstruction, a veneer, also referred to as ligament, a facette, a filling or a connector can be considered in particular as shaped dental products according to the invention which contain potassium-zinc-silicate glass or the dental material. Veneers, bridges, crowns and part-crowns are particularly preferred dental restorations.

The dental products preferably have a core based on ceramic or glass ceramic material, in particular lithium disilicate glass ceramic, to which the glass according to the invention or the dental material according to the invention is applied. Preferred lithium disilicate glass ceramics have already been described above.

In contrast to conventional glass, the glass according to the invention is even better suited in its chemical composition to apatite glass ceramics and lithium disilicate glass ceramics which are preferably used as further components of a coating material and as a substrate, respectively. The consequence of this is that precisely with thin layered composites, such as e.g. thin-walled veneers, with lithium disilicate glass ceramic as substrate to which a mixture of glass according to the invention and apatite glass ceramic has been applied, there are no signs of separation of the coating or a fracture of the finished product. The low sintering temperature of the glass according to the invention is also responsible for this advantageous behaviour.

Furthermore, the conditions prevailing during the sintering of the glass do not lead to a crystallization which would reduce its translucence in an undesired manner. Thus it essentially reproduces the colouring of the coated substrate which is advantageous in particular in case of the preparation of all-ceramic dental restorations.

In addition, the glass according to the invention shows an excellent chemical resistance which is imperative for its use as dental material around which acid liquids wash permanently in the oral cavity. It is surprising that the glass has both a good chemical resistance and a low sintering temperature. This favourable combination of properties is possibly attributable to the fact that the glass simultaneously contains several types of alkali metal ions.

The invention is explained in more detail below using examples.

EXAMPLES

Examples 1 to 34

In total, 34 different glasses according to the invention were prepared with the chemical compositions listed in Table I.

For their preparation, a corresponding amount of suitable oxides, carbonates and fluorides was melted each time in a platinum/rhodium crucible at a temperature of 1550° C. to 1600° C. for a homogenization time of 1 to 1.5 hours. The glass melt was quenched in water, and the granulate formed from the glass was dried and ground to an average particle size of less than 90 μm, relative to the number of particles.

For some of the prepared glasses, selected properties are listed in Table II which have been measured in test pieces made from the respective glass. The examples illustrate how glasses with different properties can be obtained by changing the chemical composition.

TABLE I

Composition of potassium-zinc-silicate glasses according to the invention (figures in wt %)

| Ex. | $SiO_2$ | $Li_2O$ | $K_2O$ | ZnO | $Na_2O$ | MgO | CaO | SrO | $B_2O_3$ | $Al_2O_3$ | $La_2O_3$ | $TiO_2$ | $ZrO_2$ | $SnO_2$ | $CeO_2$ | $P_2O_5$ | $Tb_4O_7$ | F |
|---|---|---|---|---|---|---|---|---|---|---|---|---|---|---|---|---|---|---|
| 1 | 63.8 | 3.7 | 18.8 | 12.7 | | | | | | | | | | | | 1.0 | | |
| 2 | 67.1 | 4.8 | 15.1 | 13.0 | | | | | | | | | | | | | | |
| 3 | 64.8 | 4.6 | 14.5 | 12.5 | | | 3.6 | | | | | | | | | | | |
| 4 | 65.0 | 4.7 | 14.7 | 12.6 | | | | | | | 3.0 | | | | | | | |
| 5 | 68.9 | 4.3 | 13.5 | 13.3 | | | | | | | | | | | | | | |
| 6 | 68.1 | 3.8 | 14.9 | 13.2 | | | | | | | | | | | | | | |
| 7 | 69.5 | 4.8 | 12.2 | 13.5 | | | | | | | | | | | | | | |
| 8 | 69.5 | 4.8 | 15.2 | 10.5 | | | | | | | | | | | | | | |
| 9 | 67.1 | 4.3 | 13.4 | 13.2 | | | | | | | | | | 2.0 | | | | |
| 10 | 65.4 | 3.7 | 14.7 | 13.0 | | | | | | | 3.2 | | | | | | | |
| 11 | 69.0 | 5.0 | 15.4 | 8.0 | | 2.6 | | | | | | | | | | | | |
| 12 | 68.1 | 4.8 | 15.1 | 8.0 | | 4.0 | | | | | | | | | | | | |
| 13 | 64.8 | 4.7 | 14.7 | 12.7 | | | | | | | | | | | 1.3 | | 1.8 | |
| 14 | 67.2 | 3.7 | 11.8 | 13.0 | | | | | | | | | 1.9 | 2.4 | | | | |
| 15 | 66.7 | 3.7 | 11.7 | 12.9 | | | | | | | | | | 5.0 | | | | |
| 16 | 65.3 | 4.7 | 14.7 | 12.7 | | | | | | | | | | | 2.0 | | 0.6 | |
| 17 | 62.0 | 1.0 | 17.0 | 20.0 | | | | | | | | | | | | | | |
| 18 | 70.6 | 3.8 | 12.0 | 13.6 | | | | | | | | | | | | | | |
| 19 | 67.5 | 3.6 | 11.3 | 13.6 | 4.0 | | | | | | | | | | | | | |
| 20 | 72.0 | 3.3 | 10.0 | 14.0 | 0.7 | | | | | | | | | | | | | |
| 21 | 64.0 | 4.0 | 12.6 | 12.4 | | | | | | 3.2 | | | 3.8 | | | | | |
| 22 | 67.1 | 4.2 | 13.2 | 13.0 | | | | | | | | | 2.5 | | | | | |
| 23 | 61.6 | 3.1 | 15.0 | 12.3 | | | | | 8.0 | | | | | | | | | |
| 24 | 60.8 | 3.7 | 23.0 | 12.5 | | | | | | | | | | | | | | |
| 25 | 60.0 | 3.7 | 23.0 | 12.5 | | | 0.8 | | | | | | | | | | | |
| 26 | 68.4 | 3.8 | 12.0 | 13.6 | | | | | 2.2 | | | | | | | | | |
| 27 | 67.8 | 3.8 | 11.9 | 13.5 | | | | 3.0 | | | | | | | | | | |
| 28 | 67.0 | 3.9 | 12.4 | 13.3 | | 2.3 | | | | | | | | | | | | 1.1 |
| 29 | 64.8 | 4.0 | 12.7 | 12.5 | 0.6 | | 3.0 | | | | | | | 1.9 | 0.5 | | | |
| 30 | 65.2 | 4.2 | 14.8 | 12.8 | 0.6 | | | | | | | | | 1.9 | 0.5 | | | |
| 31 | 61.8 | 4.1 | 14.5 | 12.5 | 0.6 | | | | | | | | | 6.0 | 0.5 | | | |
| 32 | 65.3 | 4.5 | 14.2 | 12.9 | 0.6 | | | | | | | | | 2.0 | 0.5 | | | |
| 33 | 64.5 | 4.5 | 14.2 | 12.9 | | | | | 3.3 | | | | | | 0.6 | | | |
| 34 | 65.5 | 4.6 | 14.5 | 11.3 | 0.6 | | | | 1.1 | | | | | 1.9 | 0.5 | | | |

TABLE II

Properties of potassium-zinc-silicate glasses according to the invention

| Example No. | α-value × 10$^{-6}$K$^{-1}$ [100–400° C.] | Tg [° C.] | optical behavior | firing temp. on crown [° C.] | acid resistance [μg/cm$^2$] | firing temp. for the preparation of test pieces [° C.] |
|---|---|---|---|---|---|---|
| 2  | 9.58  | 478 | transparent | 700 | 55 | 780 |
| 7  | 8.76  | 488 | transparent | 720 | 9  | 790 |
| 9  | 8.94  | 500 | transparent | 720 | 13 | 800 |
| 20 | 7.79  | 518 | transparent | 760 | 5  | 840 |
| 27 | 8.64  | 497 | transparent | 720 | 4  | 800 |
| 30 | 9.66  | 504 | transparent | 740 | 13 | 820 |
| 34 | 9.69  |     | transparent | 700 | 36 | 780 |
| 1  | 10.57 | 484 | transparent | 710 | 47 | 790 |

Measurement of the Coefficient of Expansion α

To measure the linear thermal coefficient of expansion α, a rod-shaped green body was prepared from the powder of the respective glass, and was sintered in a vacuum firing furnace at a heating-up rate of 60° C./min and with a holding time of 1 minute at the respective firing temperature for the preparation of the test pieces. Subsequently a glaze firing was carried out without vacuum at a final temperature which was 20° C. higher and with a holding time of 1 minute. The linear thermal coefficient of expansion was measured with the obtained test piece in the temperature range of 100 to 400° C.

Measurement of the Acid Resistance

The acid resistance is a measure of the chemical resistance especially of glasses and glass ceramics used in the dental field, as these are permanently exposed to the action of acid substances in the oral cavity.

The acid resistance was measured according to ISO-specification 6872:1995. To this end, small test plates with a diameter of 12 mm and a thickness of 1 mm were firstly prepared by sintering together glass powder with an average particle size of less than 90 μm. The powder was maintained for 1 minute at the relevant firing temperature for the preparation of the test pieces. Then the small test plates were treated for 16 hours with 4 vol.-% aqueous acetic acid at 80° C., and finally the loss of weight which had occurred, relative to the surface of the small plates, was determined as a measure of the acid resistance.

Example 35

This example describes the preparation of a glass according to the invention which can be used as a low-temperature-melting glazing or correcting material.

The application of a glaze layer containing glass according to the invention to a translucent lithium disilicate basic framework is particularly advantageous, as aesthetically pleasing dental restorations, e.g. in the form of inlays, onlays, part-crowns, veneers, crowns or bridges can thus be prepared. The application of a thick, multi-layered glass ceramic layer is not necessary as a result of the use of a glaze layer.

Firstly, glass powder with the composition given in Table I for example 34 was prepared analogously to the method given above for examples 1 to 34. This powder was sintered to produce a rod-shaped green body in a vacuum furnace at a heating-up rate of 60° C./minute and with a holding time of 1 minute at 780° C. Subsequently a glaze firing was carried out without a vacuum at 760° C. and with a holding time of 1 minute.

For the specimen obtained in this way, a thermal coefficient of expansion of 9.69×10$^{-6}$ K$^{-1}$ was determined, measured in the temperature range of 100 to 400° C.

This glass was therefore able to be used for sintering onto a substrate with a low coefficient of expansion of 10.6×10$^{-6}$ K$^{-1}$, such as a crown or bridge framework based on lithium disilicate glass ceramic. It is shown that the sintering of the glass onto the framework was already possible at a temperature of only 700° C.

Because the coefficient of expansion is matched to lithium disilicate glass ceramics, the very good chemical resistance and the low processing temperature, this glass according to the invention is particularly suitable for glazing very translucent frameworks based on lithium disilicate glass ceramic and also as correction material for sintering materials coated onto such frameworks.

Example 36

This example describes the use of a mixture of the glass according to the invention according to example 30 together with an apatite glass ceramic as a coating material for ceramic suprastructures and thus its usability for the preparation of all-ceramic dental products.

The apatite glass ceramic used had the composition (in wt.-%):

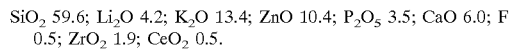
SiO$_2$ 59.6; Li$_2$O 4.2; K$_2$O 13.4; ZnO 10.4; P$_2$O$_5$ 3.5; CaO 6.0; F 0.5; ZrO$_2$ 1.9; CeO$_2$ 0.5.

For the preparation of this apatite glass ceramic, a starting glass of a corresponding composition was melted, fritted and ground into a powder. This powder was then thermally-treated for 4 hours at 520° C. and subsequently for 1 hour at 800° C.

To obtain a coating material in which sintering temperature and coefficients of expansion are suitably set, 50 wt.-% of the apatite glass ceramic was mixed with 50 wt.-% of the glass according to the invention in the form of powders with an average particle size of less than 90 μm.

This mixture was sintered to produce a rod-shaped green body in a vacuum furnace at a heating-up rate of 60° C./min and with a holding time of 1 minute at 840° C. Subsequently, a glaze firing was carried out without vacuum at 820° C. and with a holding time of 1 minute. For the test piece thus obtained, a thermal coefficient of expansion of 9.96×10$^{-6}$ K$^{-1}$ was determined, measured in the temperature range of 100° C. to 400° C.

Thus this mixture was able to be used for sintering onto a very translucent lithium disilicate glass ceramic with a thermal coefficient of expansion of $10.6 \times 10^{-6}$ K$^{-1}$. It was shown that the sintering-on of the mixture was already possible at a temperature of only 730° C. Consequently, all-ceramic dental products such as crowns or bridges, were thus able to be prepared which are characterized by an excellent bonding of the individual layers, an aesthetically pleasing appearance and good chemical resistance.

Example 37

Preparation of a Thin-walled Veneer

A thin-walled veneer for a middle upper incisor with a layer thickness of max. 0.5 mm was prepared from a lithium disilicate glass ceramic by compression in the viscous state. After the hot pressing, the layer thickness was reduced to max 0.25 mm by mechanical reworking with a diamond tool. The surface of the veneer was then cleaned in an aqueous solution of 0.5 vol.-% HF and 3 vol.-% $H_2SO_4$ for 10 minutes in an ultrasound bath and then sand-blasted with $Al_2O_3$ at a jet pressure of 1.5 bar. A dental material was then sintered on, this being a mixture of the glass 21 according to the invention and an apatite glass ceramic. The apatite glass ceramic used had the composition (in wt.-%):

$SiO_2$: 61.4; $Li_2O$: 4.3; $K_2O$: 13.6; ZnO: 10.6; $P_2O_5$: 3.5; CaO: 6.1; F: 0.5.

To prepare this glass ceramic, a starting glass of suitable composition was melted, fritted and ground to a powder. This powder was then thermally-treated for 1 hour at 800° C. To obtain a coating material in which sintering temperature and coefficient of expansion are suitably set, 50 wt.-% of the apatite glass ceramic were mixed with 50 wt.-% of the glass according to the invention in the form of powders with an average particle size of less than 90 µm. The thermal coefficient of expansion of this dental material was $9.4 \times 10^{-6}$ K$^{-1}$. The sintering temperature was 750° C. and was maintained for 1 minute during the coating of the veneer. A total of 5 firings were carried out with material application at 750° C. until the veneer was completed. The final glaze firing was carried out at 740° C. without vacuum in order to achieve a superficial inherent shine. The veneer representing a dental restoration showed a very homogeneous layer bonding. No cracks or faults formed, which is not usual with such thin-walled thicknesses. The veneer furthermore showed a very good translucence, which is an extremely important property for such a type of dental restoration.

Example 38

Preparation of a 3-Membered Front Tooth Bridge

A front tooth bridge framework with an intermediate member was prepared from a lithium disilicate glass ceramic by compression in the viscous state. The smallest wall thickness was approx. 0.5 mm. After the hot pressing, the framework was cleaned with an aqueous solution of 0.5 vol.-% HF and 3 vol.-% $H_2SO_4$ in an ultrasound bath for 10 minutes and subsequently sand-blasted with $Al_2O_3$ at a jet pressure of 1.5 bar. Then a dental material was sintered on which consisted of the glass 30 according to the invention and an apatite glass ceramic. The apatite glass ceramic used had the composition (in wt.-%):

$SiO_2$: 57.8; $Li_2O$: 4.3; $K_2O$: 13.5; ZnO: 10.5; $P_2O_5$: 3.5; CaO: 6.0; F: 0.5; MgO: 1.3; $ZrO_2$: 2.0; $CeO_2$: 0.6.

To prepare this glass ceramic, a starting glass of suitable composition was melted, fritted and ground to a powder. This powder was then thermally-treated for 4 hours at 520° C. and subsequently for 1 hour at 800° C. To obtain a coating material in which sintering temperature and coefficient of expansion are suitably set, 50 wt.-% of the apatite glass ceramic were mixed with 50 wt.-% of the glass according to the invention in the form of powders with an average particle size of less than 90 µm. The thermal coefficient of expansion of this dental material was $10.0 \times 10^{-6}$ K$^{-1}$. The sintering temperature was 730° C. and was maintained for 1 minute in each case during the coating of the framework. A total of 5 firings were carried out with material application at 730° C. until the front tooth bridge was completed. The final glaze firing was carried out at 720° C. without vacuum, in order to achieve a superficial inherent shine. The obtained three-membered tooth bridge showed a homogenous bond between lithium disilicate framework and sintering material. No cracks or faults formed in the bridge as a result of the matched coefficient of thermal expansion, the low sintering temperature and the chemical compatibility between the individual components.

What is claimed is:

1. Low-temperature-sintering potassium-zinc-silicate glass, which comprises the following components:

| Component | wt.-% |
| --- | --- |
| $SiO_2$ | 60.0 to 72.0 |
| $Li_2O$ | 1.0 to 5.0 |
| $K_2O$ | 10.0 to 23.0 |
| ZnO | 8.5 to 20.0. |

2. Glass according to claim 1, which additionally comprises at least one of the following components:

| Component | wt.-% |
| --- | --- |
| $Na_2O$ | 0 to 4.0 |
| MgO | 0 to 4.0 |
| CaO | 0 to 3.6 |
| SrO | 0 to 3.0 |
| $Al_2O_3$ | 0 to 8.0 |
| $B_2O_3$ | 0 to 3.3 |
| $La_2O_3$ | 0 to 3.0 |
| $ZrO_2$ | 0 to 6.0 |
| $TiO_2$ | 0 to 2.5 |
| $CeO_2$ | 0 to 2.0 |
| $SnO_2$ | 0 to 5.0 |
| $P_2O_5$ | 0 to 1.0 |
| $Tb_4O_7$ | 0 to 1.8 |
| F | 0 to 1.1. |

3. Glass according to claim 2, wherein the amounts of components are selected independently of each other and are as follows:

| Component | wt.-% |
| --- | --- |
| $SiO_2$ | 62.0 to 70.0 |
| $Li_2O$ | 2.0 to 5.0 |
| $K_2O$ | 10.0 to 20.0 |
| ZnO | 10.0 to 19.0 |
| $Na_2O$ | 0 to 3.0 |
| MgO | 0 to 3.0 |
| CaO | 0 to 3.0 |
| SrO | 0 to 3.0 |
| $Al_2O_3$ | 0 to 6.0 |

-continued

| Component | wt.-% |
|---|---|
| $B_2O_3$ | 0 to 3.0 |
| $La_2O_3$ | 0 to 2.0 |
| $ZrO_2$ | 0 to 5.0 |
| $TiO_2$ | 0 to 2.0 |
| $CeO_2$ | 0 to 1.5 |
| $SnO_2$ | 0 to 4.0 |
| $P_2O_5$ | 0 to 0.8 |
| $Tb_4O_7$ | 0 to 1.0 |
| F | 0 to 1.0. |

4. Glass according to claim 2, wherein the amounts of components are selected independently of each other and are as follows:

| Component | wt.-% |
|---|---|
| $SiO_2$ | 63.0 to 69.0 |
| $Li_2O$ | 3.0 to 5.0 |
| $K_2O$ | 11.0 to 19.0 |
| ZnO | 10.0 to 17.0 |
| $Na_2O$ | 0 to 2.5 |
| MgO | 0 to 2.5 |
| CaO | 0 to 2.5 |
| SrO | 0 to 2.5 |
| $Al_2O_3$ | 0 to 4.0 |
| $B_2O_3$ | 0 to 2.0 |
| $La_2O_3$ | 0 to 1.8 |
| $ZrO_2$ | 0 to 4.0 |
| $TiO_2$ | 0 to 1.8 |
| $CeO_2$ | 0.1 to 1.5 |
| $SnO_2$ | 0 to 3.5 |
| $P_2O_5$ | 0 to 0.5 |
| $Tb_4O_7$ | 0 to 0.8 |
| F | 0 to 0.8. |

5. Glass according to claim 1, which does not crystallize during thermal treatment in the range of 600° C. to 800° C. for 1 minute to 1 hour.

6. Glass according to claim 1, which has a sintering temperature of less than 800° C.

7. Glass according to claim 1, which has a linear thermal coefficient of expansion of less than $12.3 \times 10^{-6}$ $K^{-1}$, measured in the range of 100° C. to 400° C.

8. Dental material, which comprises the glass according to claim 1.

9. Dental material according to claim 8, which has a sintering temperature of less than 800° C.

10. Dental material according to claim 8, which additionally comprises an apatite glass ceramic.

11. Dental material according to claim 10, wherein the apatite glass ceramic comprises the following components and the main crystal phase is formed by apatite crystals:

| Component | wt.-% |
|---|---|
| $SiO_2$ | 56.0 to 65.0 |
| $Li_2O$ | 1.8 to 5.3 |

-continued

| Component | wt.-% |
|---|---|
| $K_2O$ | 9.0 to 17.5 |
| ZnO | 9.0 to 16.0 |
| CaO | 3.5 to 10.5 |
| $P_2O_5$ | 2.0 to 6.0 |
| F | 0.5 to 1.0. |

12. A method for coating comprising coating a substrate with the dental material according to claim 8.

13. The method according to claim 12, wherein the dental material is applied to the substrate, optionally shaped in the desired manner, and then sintered, in order to produce a coating adhering firmly to the substrate.

14. The method according to claim 12, wherein said material comprises ceramic, glass ceramic material, or titanium.

15. The method according to claim 14, wherein the glass ceramic material is a lithium disilicate glass ceramic which comprises the following components:

| Component | wt.-% |
|---|---|
| $SiO_2$ | 57.0 to 80.0 |
| $Al_2O_3$ | 0 to 5.0 |
| $La_2O_3$ | 0.1 to 6.0 |
| MgO | 0 to 5.0 |
| ZnO | 0 to 8.0 |
| $Li_2O$ | 11.0 to 19.0 |
| $P_2O_5$ | 0 to 11.0. | where
(a) $Al_2O_3+La_2O_3$ account for 0.1 to 7.0 wt.-% and
(b) MgO+ZnO account for 0.1 to 9.0 wt.-%.

16. The method according to claim 14, wherein the ceramic material is a $ZrO_2$ ceramic, $Al_2O_3$ ceramic, $ZrO_2/Al_2O_3$ ceramic, or ceramic composite material.

17. The method according to claim 13, wherein the dental material is applied t the substrate and sintered at temperatures of less than 800° C.

18. Shaped dental product, which comprises potassium-zinc-silicate glass according to claim 1.

19. Shaped dental product according to claim 18, which is a dental restoration.

20. Shaped dental product according to claim 18, which has a core based on ceramic or glass ceramic material and a coating applied to it which comprises the potassium-zinc-silicate glass.

21. Shaped dental product according to claim 20, wherein the glass ceramic material is a lithium disilicate glass ceramic.

22. Glass according to claim 1, which has a sintering temperature of 760° C. or less.

23. Dental material according to claim 8, which has a sintering temperature of 760° C. or less.

24. The method according to claim 12, wherein said substrate comprises a dental restoration.

* * * * *